(12) United States Patent
Namiki et al.

(10) Patent No.: US 9,560,962 B2
(45) Date of Patent: Feb. 7, 2017

(54) OPTICAL TOMOGRAPHIC IMAGE PHOTOGRAPHING APPARATUS AND OPTICAL TOMOGRAPHIC IMAGE PHOTOGRAPHING PROGRAM

(71) Applicant: NIDEK CO., LTD., Gamagori, Aichi (JP)

(72) Inventors: Hajimi Namiki, Aichi (JP); Junpei Nishiyama, Aichi (JP); Natsuru Misaki, Aichi (JP)

(73) Assignee: NIDEK CO., LTD., Aichi (JP)

( * ) Notice: Subject to any disclaimer, the term of this patent is extended or adjusted under 35 U.S.C. 154(b) by 0 days.

(21) Appl. No.: 14/556,583

(22) Filed: Dec. 1, 2014

(65) Prior Publication Data

US 2015/0182111 A1    Jul. 2, 2015

(30) Foreign Application Priority Data

Nov. 29, 2013  (JP) ................. 2013-248734

(51) Int. Cl.
*A61B 3/14* (2006.01)
*A61B 3/10* (2006.01)
*A61B 3/00* (2006.01)

(52) U.S. Cl.
CPC .......... *A61B 3/102* (2013.01); *A61B 3/0025* (2013.01); *A61B 3/0041* (2013.01); *A61B 3/14* (2013.01)

(58) Field of Classification Search
USPC ................................. 351/200–246
See application file for complete search history.

(56) References Cited

U.S. PATENT DOCUMENTS

| 2005/0168751 A1 | 8/2005 | Horii et al. | |
| 2009/0012397 A1* | 1/2009 | Matsushita | A61B 8/08 600/443 |
| 2014/0204341 A1* | 7/2014 | Murase | A61B 3/102 351/208 |

FOREIGN PATENT DOCUMENTS

JP    2000-131222 A    5/2000

* cited by examiner

*Primary Examiner* — Mohammed Hasan
(74) *Attorney, Agent, or Firm* — Sughrue Mion, PLLC

(57) ABSTRACT

An optical tomographic image photographing apparatus for acquiring information on a tissue inside a specimen, the apparatus includes: a synthesis unit configured to generate a interference beam by synthesizing a measuring beam reflected from the tissue and a reference beam; and a detector configured to detect the generated first interference beam as a first interference signal, the first interference beam being detected for each scanning position of the measuring beam. The optical tomographic image photographing apparatus acquires tomographic information for each scanning position of the specimen by using the detected first interference signal and acquiring tomographic image data of the specimen expressed by polar coordinates by using the tomographic information; and converts the tomographic image data of the specimen expressed by the acquired polar coordinates into image data expressed by rectangular coordinates.

6 Claims, 6 Drawing Sheets

OPTICAL TOMOGRAPHIC IMAGE PHOTOGRAPHING APPARATUS AND OPTICAL TOMOGRAPHIC IMAGE PHOTOGRAPHING PROGRAM

CROSS REFERENCE TO RELATED APPLICATION

This application is based upon and claims the benefit of priority of Japanese Patent Application No. 2013-248734 filed on Nov. 29, 2013, the contents of which are incorporated herein by reference in its entirety.

BACKGROUND

The present invention relates to an optical tomographic image photographing apparatus which photographs a tomographic image of a tissue of a specimen, and an optical tomographic image photographing program.

In the related art, as an apparatus which is capable of photographing a tomographic image in a predetermined portion of a specimen, an apparatus employing an optical coherence tomography (OCT) has been known. An optical tomographic image photographing apparatus which employs the OCT divides the light beam emitted from a light source into a measuring beam and a reference beam and the irradiates tissue of the specimen with the divided measuring beam. The measuring beam reflected from the tissue is synthesized with the reference beam, and the information on the tissue in the depth direction is acquired through the interference signal of the synthesized light. The optical tomographic image photographing apparatus can generate the tomographic image by using the acquired information of the tissue in the depth direction.

An optical tomographic image photographing apparatus which photographs the tomographic image of the tissue in the specimen by emitting the measuring beam from a tip end of a probe which can be inserted into the specimen has been proposed. In such an optical tomographic image photographing apparatus, the specimen is scanned with the measuring beam by the rotation of an optical fiber in the probe and thereby the image data is acquired by a detector for each scanning angle set in advance (for example, JP-A-2000-131222).

SUMMARY

Meanwhile, the image data acquired by rotation of the optical fiber is a collection of primary image data regulated by a polar coordinate system. The tomographic image (the image data expressed by polar coordinates) is generated by assuming a horizontal axis to be the scanning angle ($\theta$) and arranging the primary image data items in a line for each scanning line. The tomographic image generated in this manner is different from the form (shape) of an actual fundus of an eye. For this reason, for example, the length is different from the actual length, and thus it is difficult to measure the thickness of an optic stratum in some cases.

The present invention was made in consideration of the above described circumstance, and an object thereof is to provide an optical tomographic image photographing apparatus and an optical tomographic image photographing program capable of acquiring useful information for diagnosing an object eye.

In order to solve the above problems, the present invention includes the following configurations.

(1) An optical tomographic image photographing apparatus for acquiring information on a tissue inside a specimen in a depth direction, the apparatus comprising:
a light source configured to emit a light beam;
a dividing unit configured to divide the emitted optical flux into a measuring beam and a reference beam;
a attaching unit to which a probe is to be attached, the probe being configured to irradiate an inside of the specimen with the measuring beam and rotatably scan the inside of the specimen with the measuring beam;
a synthesis unit configured to generate a first interference beam by synthesizing the measuring beam reflected from the tissue inside the specimen and the reference beam;
a detector configured to detect the generated first interference beam as a first interference signal, the first interference beam being detected for each scanning position of the measuring beam;
a processor; and
memory storing a computer executable program, when executed by the processor, causing the optical tomographic image photographing apparatus to execute:
a tomographic image acquiring instruction of acquiring tomographic information for each scanning position of the specimen by using the detected first interference signal and acquiring tomographic image data of the specimen expressed by polar coordinates by using the tomographic information; and
a coordinate conversion instruction of converting the tomographic image data of the specimen expressed by the acquired polar coordinates into image data expressed by rectangular coordinates.

A computer readable recording medium storing a program for an optical tomographic image photographing apparatus which acquires information on a tissue inside a specimen in a depth direction, the optical tomographic image photographing apparatus including: a attaching unit to which the probe is attached; a synthesis unit configured to generate a first interference beam by synthesizing the measuring beam reflected from the tissue inside the specimen and the reference beam; a detector configured to detect the generated first interference beam as a first interference signal, the first interference beam being detected for each scanning position of the measuring beam; and a processor, the program when executed by the processor causing the optical tomographic image photographing apparatus to execute:
a tomographic image acquiring instruction of acquiring tomographic information for each scanning position of the specimen by using the detected first interference signal and acquiring tomographic image data of the specimen expressed by polar coordinates by using the tomographic information; and
a coordinate conversion instruction of converting the tomographic image data of the specimen expressed by the acquired polar coordinates into image data expressed by rectangular coordinates.

DESCRIPTION OF ILLUSTRATIVE EMBODIMENTS

<Outline>

Figure 1:
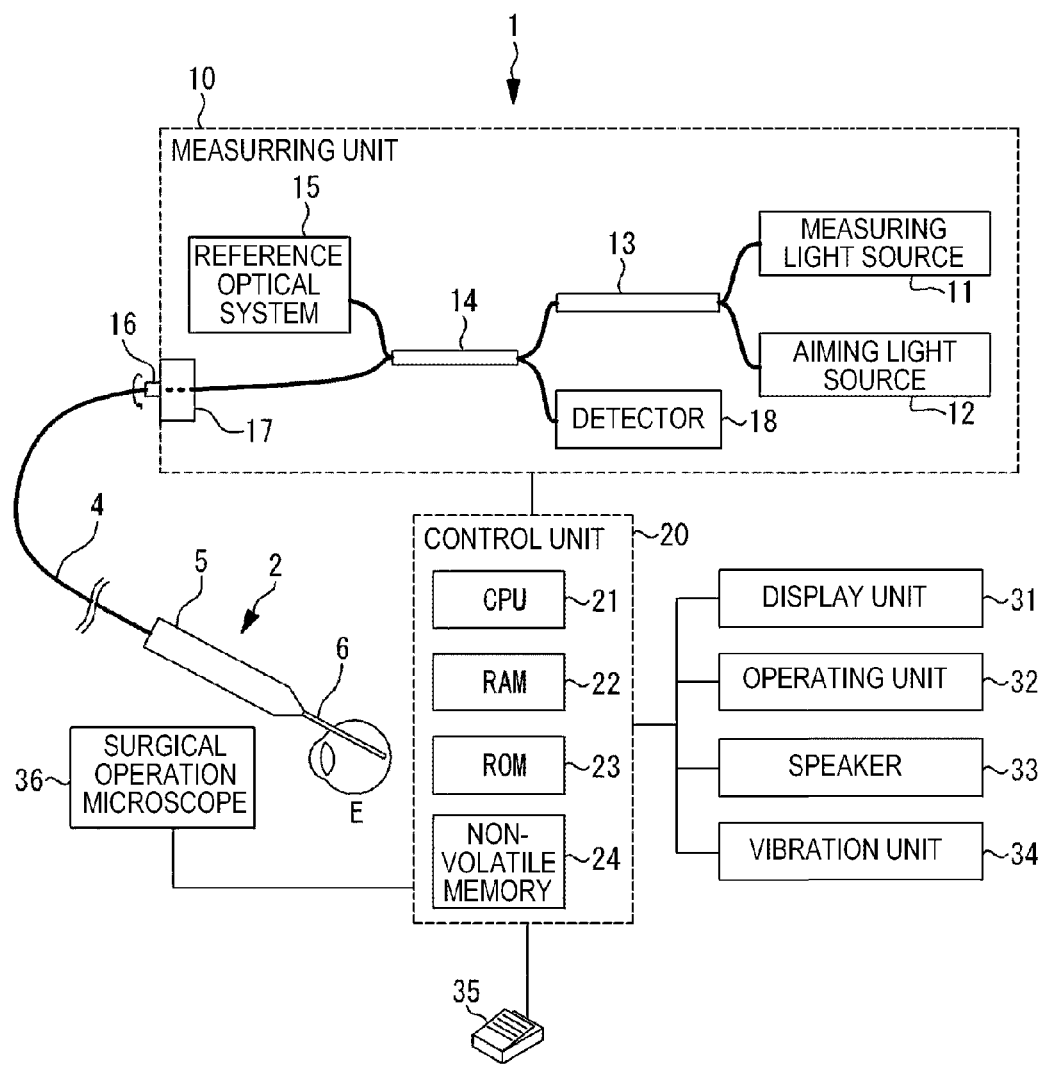
FIG. 1 is a configuration view schematically illustrating an optical tomographic image photographing apparatus and peripheral devices.

The outline of the present example will be described. An optical tomographic image photographing apparatus 1 of the example acquires information on a tissue inside a specimen in a depth direction. The optical tomographic image photographing apparatus 1 mainly includes dividing means (for example, a coupler 14), a attaching unit 16, synthesis means (for example, the coupler 14), a detector 18, tomographic image acquiring means (for example, a control unit 20 and a CPU 21), and coordinate conversion means (for example, the control unit 20 and the CPU 21).

The dividing means divides an optical flux emitted from a light source into a measuring beam and a reference beam. The attaching unit mounts a probe 2 irradiating an inside of a specimen with the measuring beam divided by the dividing means and rotatably scanning the inside of the object with the measuring beam thereon. Here, "rotatably scanning" includes a case of the rotary scanning with the measuring beam performed by rotating an optical member (a fiber 4 and the like) in the probe 2 around a shaft of the probe 2 and the rotary scanning performed by an optical scanner which is provided at a tip end of the probe 2.

The synthesis means generates an interference beam by synthesizing the measuring beam (a first measuring beam) which is emitted from the probe 2 and reflected from the inside of the specimen and the reference beam divided by the dividing means.

The detector 18 detects the interference beam generated by synthesizing the first measuring beam and the reference beam by the synthesis means as a first interference signal for each scanning position of the measuring beam. For example, the interference beam is detected for each scanning angle of the measuring beam.

The tomographic image acquiring means acquires tomographic information for each scanning position of the specimen by using the first interference signal detected by the detector 18 and tomographic image data of the specimen expressed by polar coordinates by using the tomographic information.

The coordinate conversion means converts the tomographic image data of the specimen expressed by the polar coordinates acquired by the tomographic image acquiring means into image data expressed by rectangular coordinates.

The apparatus 1 converts an image expressed by polar coordinates into an image expressed by rectangular coordinates. Accordingly, it is possible for the specimen in reality to have the same form as that of the specimen in the image.

In addition, when the image data expressed by the polar coordinates is converted into the image data expressed by rectangular coordinates, the apparatus may perform the conversion of the image data on the basis of the position of a rotation axis when the inside of the specimen is rotatably scanned with the measuring beam. For example, the image data may be converted by setting the position of the rotation axis as an origin of a polar coordinates system when the inside of the specimen is rotatably scanned with the measuring beam.

In this case, for example, the synthesis means may generate the interference beam obtained by synthesizing the measuring beam (a second measuring beam) which is emitted from the light source and reflected from the inside of the probe without being applied to the inside of the specimen and the reference beam divided by the dividing means. In addition, the interference beam may be detected as a second interference signal. The tomographic image acquiring means may acquire the positional information of the inside of the probe from which the measuring beam is reflected by using the second interference signal detected by the detector 18. The coordinate conversion means may acquire a shaft position of a rotation axis when the probe rotatably scans the inside of the specimen with the measuring beam by using the positional information on the inside of the probe which is acquired by the tomographic image acquiring means. Then, the coordinate conversion means may convert the tomographic image data of the specimen expressed by the polar coordinates into tomographic image data expressed by the rectangular coordinates by setting the position of the acquired rotation axis as an origin of a polar coordinates system.

Meanwhile, the probe 2 may include an optical fiber (referred to as a fiber in some cases) 4 and a shielding member inside thereof. The fiber 4 guides the measuring beam emitted from the light source of the apparatus 1 to the specimen. The shielding member (for example, an external cylinder 61) is an optical member shielding the measuring beam emitted from the optical fiber 4. In this case, the synthesis means may synthesize the measuring beam, as the second measuring beam, reflected from the shielding member and the reference beam. The detector 18 may detect the interference beam obtained by synthesizing the measuring beam reflected from the shielding member and the reference beam as the second interference signal. The coordinate conversion means may acquire the positional information of the optical member (the shielding member or the like) from which the measuring beam is reflected through the second interference signal. Then, the coordinate conversion means may acquire the shaft position of the rotation axis when the probe 2 rotatably scans the inside of the specimen with the measuring beam by using the positional information of the optical member from which the measuring beam is reflected. Further, the coordinate conversion means may perform the conversion of the tomographic image data of the specimen by setting the acquired shaft position of the rotation axis as an origin of a polar coordinates system.

In addition, the probe 2 may include the optical member which is coupled with the optical fiber 4 and guides the measuring beam emitted from the fiber to the inside of the specimen in the inside thereof. In addition, the detector 18 may detect, as a second interference signal, the interference beam obtained by synthesizing the measuring beam (second measuring beam) which is reflected from an interface between the fiber 4 and the optical member and the reference beam divided by the dividing means by the synthesis means.

Meanwhile, the apparatus 1 may be provided with distance calculating means. The distance calculating means may calculate the distance between two points in the specimen based on the tomographic image data which is coordinate-converted by the coordinate conversion means.

Note that, the apparatus 1 may include a display unit 31 and display control means (for example, the control unit 20). The display unit 31 displays the tomographic image. The display control means causes the display unit to display the tomographic image data as the tomographic image. In addition, the display control means may cause the display unit to display the tomographic image data, coordinate-converted into the rectangular coordinates by the coordinate conversion means, as the tomographic image.

Meanwhile, the control unit 20 may include a processor (for example, the CPU 21) for controlling a variety of control processes and a storage medium for storing a program. The processor may cause the optical tomographic image photographing apparatus 1 to execute a dividing step, a rotary scanning step, a synthesizing step, a detecting step, a tomographic image acquiring step, a coordinate conversion step or the like. The dividing step divides the optical flux emitted from the light source into the measuring beam and the reference beam. The rotary scanning step causes the probe 2 to irradiate the inside of the specimen with the measuring beam divided in the dividing step and rotatably scanning the inside of the specimen with the measuring beam. The synthesizing step generates the interference beam by synthesizing the measuring beam which is emitted from the probe 2 and is reflected from the tissue inside the specimen and the reference beam which is divided in the dividing step. The detecting step detects the interference beam generated in the synthesizing step as the first interference signal for each scanning position of the measuring beam. The tomographic image acquiring step acquires tomographic information for each scanning position of the specimen through the first interference signal detected in the detecting step and tomographic image data of the specimen expressed by polar coordinates by using the tomographic information. The coordinate conversion step converts the tomographic image data of the specimen expressed by the polar coordinates acquired in the tomographic image acquiring step into image data expressed by rectangular coordinates.

Example

Hereinafter, description is given of an example of the present invention with reference to the drawings. First, a schematic configuration of an optical tomographic image photographing apparatus 1 according to the present embodiment is described with reference to FIG. 1. The optical tomographic image photographing apparatus (an optical coherence tomographic device) 1 of the embodiment photographs a tomographic image of a tissue inside the specimen by using a probe 2 being inserted into the specimen. According to the embodiment, the description is made by exemplifying an ophthalmologic photographing apparatus which photographs the tomographic image of the tissue (for example, the retina) inside an object eye E. However, the present invention may be applied to an apparatus which photographs tomographic images of specimens (for example, internal organs or an ear) other than an eye. The optical tomographic image photographing apparatus 1 includes a measuring unit 10 and a control unit 20.

The measuring unit 10 is configured to have an optical coherence tomography (OCT). The measuring unit 10 of the present embodiment includes a measuring light source 11, an aiming light source 12, a coupler 13, the coupler 14, a reference optical system 15, the attaching unit 16, a fiber rotation motor 17, and the detector (a light receiving element) 18.

The measuring light source 11 emits light so as to acquire a tomographic image. As an example, the optical tomographic image photographing apparatus 1 of the embodiment acquires the tomographic image through a Swept-source OCT (SS-OCT) measurement by including the measuring light source 11 which is capable of changing the wavelength of a laser beam to be emitted at a high speed. The measuring light source 11 of the embodiment is configured to have a laser medium, a resonator, a wavelength selection filter, or the like. As the wavelength selection filter, for example, a combination of a diffraction grating and a polygon mirror, or a filter using Fabry-Perot etalon is employed.

The aiming light source 12 emits an aiming beam which is visible light for indicating an irradiation position of a measuring beam (in other words, an acquiring position of information in the depth direction, or a photographing position of the tomographic image when photographing the tomographic image). The aiming light source 12 of the embodiment can cause a color of the aiming beam (the wavelength) to change within a range from green to red. In addition, the aiming light source 12 can cause a period of flashing of the aiming beam to vary by switching between flashing of the aiming beam and constant lighting.

The coupler 13 combines a light beam emitted from the measuring light source 11 and the aiming beam emitted from the aiming light source 12 so as to coincide optical axes of the two light beams with each other. The coupler 14 divides the light from the coupler 13 into the measuring beam (sample light) and the reference beam. The measuring beam is wave-guided to the probe 2 which is attached to the attaching unit 16. A reference beam is wave-guided to the reference optical system 15. In addition, the coupler 14 generates an interference beam by synthesizing the measuring beam (a reflected measuring beam) reflected from the object eye E and the reference beam generated by the reference optical system 15. The coupler 14 causes the generated interference beam to be received in the detector 18.

The reference optical system 15 returns the reference beam which is wave-guided by the coupler 14 to the coupler 14. The reference optical system 15 may be a Michelson type or may be a Mach-Zehnder type. According to the embodiment, the reference optical system 15 causes the reference beam guided from the coupler 14 to be reflected from a reflecting optical system including a reference mirror or the like so as to return the reference beam to the coupler 14. As described above, the reference beam which is returned to the coupler 14 is synthesized with the reflected measuring beam which is reflected from the object eye E. The configuration of the reference optical system 15 can be changed. For example, the reference optical system 15 may cause the reference beam guided from the coupler 14 not to be reflected but be transmitted to the detector 18 by a transmission optical system such as the optical fiber.

A rear end portion (a base end portion) of the fiber 4 in the probe 2 is detachably attached to the attaching unit (for example, a connector) 16. The probe 2 of the embodiment includes the fiber 4, a handpiece 5, and an insertion portion (for example, a needle) 6. The fiber 4 wave-guides the measuring beam and the aiming beam guided from the coupler 14 of the measuring unit 10 to the tip end of the insertion portion 6. The fiber 4 is coated with a torque coil (not shown) and is rotatable with respect to the handpiece 5. The handpiece 5 is a substantially cylinder-shaped member which is grasped by an operator (for example, an inspector or a technician). The insertion portion 6 is provided at a tip end of the handpiece 5 and has an outer diameter smaller than the outer diameter of the handpiece 5. The tip end of the insertion portion 6 is inserted into the specimen (for example, the object eye E). The fiber 4 is connected to a rear end portion of the handpiece 5 and extends to the tip end of the insertion portion 6. The probe 2 can emit the measuring beam and the aiming beam which are wave-guided by the fiber 4 from the tip end thereof while scanning the specimen with the measuring beam and the aiming beam. The description for a structure of the tip end in the probe 2 will be made in detail with reference to FIG. 2.

The fiber rotation motor 17 can cause the attaching unit 16 to which the fiber 4 in the probe 2 is attached to rotate around an axis of the fiber 4. In other words, the fiber rotation motor 17 causes the attaching unit 16 to rotate with the fiber 4, and thus the scanning is performed with the measuring beam and the aiming beam.

The detector 18 detects an interference state between the reflected measuring beam and the reference beam. In other words, the detector 18 detects an interference signal of the interference beam generated by the coupler 14. More specifically, in a case of a Fourier domain OCT, spectrum intensity of the interference beam is detected by the detector 18 and then a depth profile (a scan signal A) in a predetermined range is acquired through a Fourier transform with respect to data of the spectrum intensity. As described above, the optical tomographic image photographing apparatus 1 of the embodiment employs an SS-OCT. However, the optical tomographic image photographing apparatus 1 may employ various types of OCTs. For example, any one of a Spectral-domain OCT (SD-OCT), a Time-domain OCT (TD-OCT), and the like may be employed in the optical tomographic image photographing apparatus 1. In a case where the SS-OCT is employed, it is preferable that a balanced detector including a plurality of light receiving elements be employed as the detector 18. When the balanced detector is used, the optical tomographic image photographing apparatus 1 can obtain a difference of interference signals from the plurality of light receiving elements, and thus it is possible to reduce unnecessary noise included in the interference signal. As a result, a quality of the tomographic image is improved.

Meanwhile, the measuring unit 10 is configured to change an optical path length difference between the measuring beam and the reference beam. The measuring unit 10 of the present embodiment changes the optical path length difference by moving the optical member (for example, the reference mirror) included in the reference optical system 15 in the optical axis direction. Here, the configuration for changing the optical path length difference may be disposed in the middle of the optical path of the measuring beam. In addition, the optical tomographic image photographing apparatus 1 further includes a variety of configurations such as an optical system for performing focus adjustment of the measuring beam, but the description thereof will not be made.

The control unit 20 includes the CPU (a processor) 21, a RAM 22, a ROM 23, a non-volatile memory 24, or the like. The CPU 21 controls the optical tomographic image photographing apparatus 1 and peripheral devices. The RAM 22 temporarily stores a variety of information. In the ROM 23, a variety of programs, an initial value, and the like are stored. The non-volatile memory 24 is a non-transitory storage medium capable of saving the stored contents even when the power supply is cut off. For example, a hard disk drive, a flash ROM, and a USB memory which is detachably mounted on the optical tomographic image photographing apparatus 1 can be used as the non-volatile memory 24. A photographing control program for controlling a process executed by the CPU 21 is stored in the non-volatile memory 24. In addition, in the non-volatile memory 24, a variety of information such as a photographed tomographic image and the distance between a tip end of the probe 2 and a tissue is stored.

According to the embodiment, a personal computer (hereinafter, referred to as "PC") connected to the measuring unit 10 is used as the control unit 20. However, without using the PC, the measuring unit 10 and the control unit 20 may be integrally formed as one device. In addition, the control unit 20 may be configured of a plurality of control units (that is, a plurality of processors). For example, the control unit 20 of the optical tomographic image photographing apparatus 1 may be configured of a first control unit provided in the PC and a second control unit provided inside the measuring unit 10. In this case, for example, the first control unit provided in the PC may instruct the second control unit to perform the start and end of the photographing based on an operation of an operating unit connected to the PC. The second control unit may control operations of the measuring light source 11, the aiming light source 12, the fiber rotation motor 17, or the like following instructions from the first control unit. In addition, an image generating process or the like based on the interference signal may be performed in both of the first control unit and the second control unit.

The peripheral devices, such as a display unit 31, an operating unit 32, a speaker 33, a vibration unit 34, a foot switch 35, and a surgical operation microscope 36 are electrically connected to the control unit 20. A screen for work (not shown) or the like is displayed on the display unit 31. The display unit 31 may be a display unit of the PC or may be a dedicated display unit for the optical tomographic image photographing apparatus 1. Alternately, a plurality of display units may be used in combination. The operating unit 32 is a device for identifying a variety of instructions for operations by an operator. As for the operating unit 32, for example, at least any one of a mouse, a joy-stick, a keyboard, a touch panel, and the like may be used. The speaker 33 generates sounds. The vibration unit 34 can generate vibration which is felt by an operator.

The foot switch 35 is disposed at an operator's feet. The operator can operate the foot switch 35 while observing the probe 2 or the like. The surgical operation microscope 36 magnifies and displays (by photographing in the embodiment) the inside of the specimen (the object eye E in the embodiment) during surgery or diagnosis, or during the training thereof. The operator performs the surgery or the diagnosis, or the training thereof (according to the embodiment, these are collectively referred to as "operation") while looking into the surgical operation microscope 36. In addition, according to the embodiment, the control unit 20 can acquire the image photographed by the surgical operation microscope 36 so as to display the image on the display unit 31. During operation, an assistant or the like of the operator can check an operation state or the like through the image displayed on the display unit 31. Note that, it is possible to realize the present invention without using the surgical operation microscope 36. For example, an observation optical system for photographing the image inside the specimen may be provided in the measuring unit 10. In this case, the operator can operate while checking the image photographed by the observation optical system. Further, the present invention is applied to a case where the operator observes the proximity of the tip end of the probe 2 by the naked eye.

Figure 2:
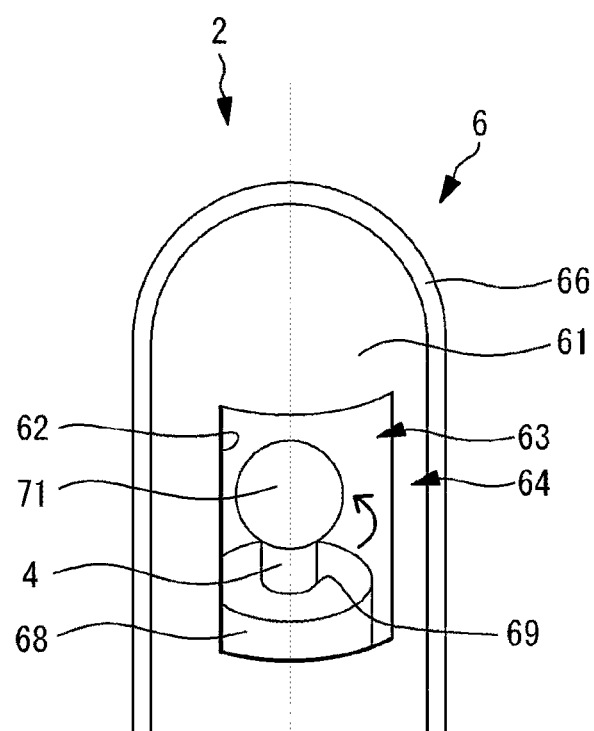
FIG. 2 is an enlarged view of the proximity of a tip end of a probe.

With reference to FIG. 2, a structure of the tip end of the insertion portion 6 of the probe 2 will be described in detail. An external cylinder 61, a cover 66, a holding portion 68, a condensing portion 71 and the like are provided in the tip end of the insertion portion 6.

The external cylinder 61 covers the periphery of the tip end of the fiber 4 (particularly, in the periphery of the holding portion 68 and the condensing portion 71). According to the embodiment, a shape of an external cylinder 61 is a substantially cylindrical shape having a hemispherical occluding part at the tip end. The external cylinder 61 is formed of a material having a function of shielding the measuring beam and the aiming beam. In the external cylinder 61, an opening 62, which has the predetermined width in the scanning direction (the direction around the axis) of the measuring beam and the aiming beam, is formed in the proximity of a portion at which the condensing portion 71 is positioned in the axial direction. The optical flux is emitted from the condensing portion 71 is transmitted to the outside in an area 63 (hereinafter, referred to as "a transmission area 63") inside the opening 62, but is shielded by the external cylinder 61 in an area 64 (hereinafter, referred to as "a shielding area 64") where the opening 62 is not formed.

According to the embodiment, an inner surface of the external cylinder 61 is subjected to a roughing process. In other words, a large number of minute irregularities are formed in the inner surface of the external cylinder 61. In this case, the light applied to the inner surface of the external cylinder 61 is scattered in the shielding area 64. Accordingly, the reflected light reflected from the shielding area 64 is less likely to return to the condensing portion 71 compared with a case where the light is not easily scattered in the inner surface of the external cylinder 61 (for example, the inner surface is subjected to a polishing process). In other words, in a case of being subjected to the polishing process or the like, if the light is reflected toward a different direction from the condensing portion 71, the reflected light is not incident on the condensing portion 71. When the reflected light is scattered, the reflected light is easily returned to the condensing portion 71. Therefore, the optical tomographic image photographing apparatus 1 can perform more reliable detection by using the reflected light reflected from the shielding area 64 when detecting a state where the shielding area 64 is irradiated with the measuring beam.

Meanwhile, a shape of the transmission area 63 of the embodiment is substantially rectangular, but needless to say, a size, a shape, the number, or the like of the transmission area 63 can be changed. In addition, a specific method for forming the transmission area 63 and the shielding area 64 can be also changed. For example, the transmission area 63 and the shielding area 64 may be formed by combining a material transmitting the measuring beam and the aiming beam and a material shielding the measuring beam and the aiming beam for manufacturing the external cylinder 61.

The cover 66 is formed of the material transmitting the measuring beam and aiming beam and blocks the outside of the external cylinder 61. Accordingly, the cover 66 allows the light transmission to be performed between the inside and the outside of the transmission area 63 while preventing blood, a tissue of vitreous body, or the like from intruding inside the external cylinder 61 from the opening 62. Meanwhile, the cover 66 may be positioned on the inner side of the external cylinder 61. In addition, the cover 66 may be configured to block only the opening 62 of the external cylinder 61.

A holding portion 68 is a member having a substantially cylindrical outer shape and is fixed with respect to the external cylinder 61. An insertion hole 69 which inserts the fiber 4 being in a rotatable state is formed in a center portion of a shaft of the holding portion 68. The holding portion 68 holds the fiber 4 to be rotatable in a state where the position of the fiber 4 on the shaft with respect to the external cylinder 61 is constant.

The condensing portion 71 is provided in the tip end of the fiber 4. The condensing portion 71 causes the light beam emitted from the tip end of the fiber 4 to be deflected and concentrated on the tissue of the specimen. In addition, the reflected measuring beam reflected from the tissue is received in the condensing portion 71 and incident on the fiber 4. The condensing portion 71 of the present embodiment causes the light beam to be deflected at an angle of about 70° with respect to the fiber 4 in the axial direction, but the deflection angle can be properly changed. Meanwhile, in the fiber 4, a shaft 73 serving for suppression of a distortion or the like of the fiber 4 is provided in the outer periphery of a portion on the rear end side from the holding portion 68.

Figure 3:
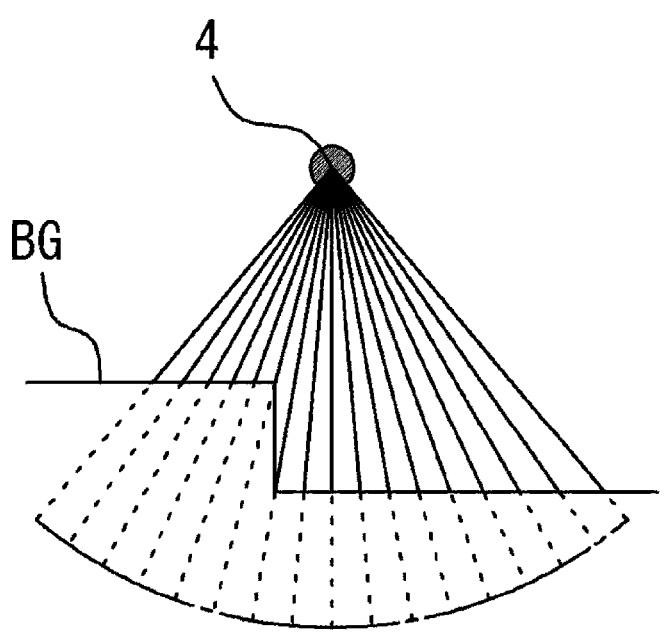
FIG. 3 is a schematic view for explaining the scanning of the measuring beam in the present example.
Figure 4A:
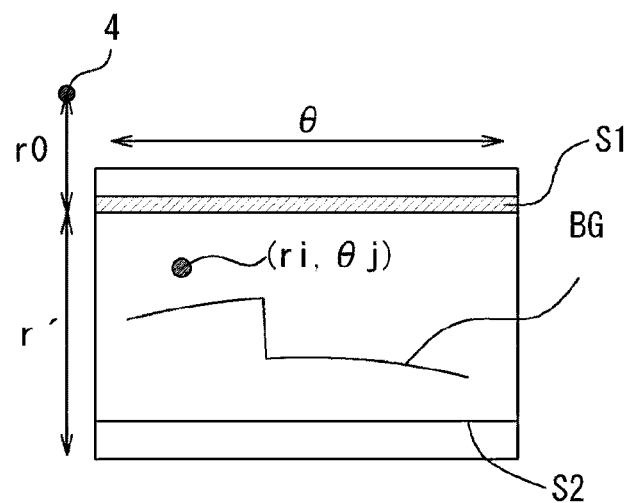
FIGS. 4A and 4B are diagrams for explaining an image acquired in the example.

FIG. 3 is a diagram illustrating a state of scanning when measuring, for example, a horizontal step (for example, block gauge BG) by the optical tomographic image photographing apparatus 1 in the embodiment. When data acquired by the rotary scanning as illustrated in FIG. 3 is imaged, an image is generated by arranging data items, acquired at scanning angles as illustrated in FIG. 4A, in a line. In this manner, the image data expressed by the polar coordinates is displayed in a different form from the actual. For example, a flat one is displayed to be largely curved and a resolution of a horizontal pixel is changed depending of the depth. As illustrated in FIG. 4A, the horizontal step ends up being curved. In this way, with the image data expressed by the polar coordinates, an inspector cannot observe a tomographic shape of the retina in actuality and thus it is difficult to measure the distance on the image.

Accordingly, according to the embodiment, by coordinates-converting the image acquired from the polar coordinates system into the rectangular coordinates system, the data is converted into the same image as that of the actual form of the specimen. Therefore, an intuitively understandable display is realized. In addition, the tomographic image which is coordinate-converted into the rectangular coordinates system is advantageous in measuring the length (the distance) of a portion of the specimen (described later in detail).

<Table for Conversion>

Hereinafter, as an example of an image processing method of the present example, a method of creating a table for conversion so as to coordinates-convert the tomographic image acquired by the polar coordinates system into the rectangular coordinates will be described. In the example, the image conversion is performed by calculating the polar coordinates corresponding to the coordinates system of the image (for example, the rectangular coordinates system) to be calculated and then performing an interpolation from the original image.

For example, the table for conversion is created by identifying which pixel (xi, yj) configuring the image data (hereinafter, referred to as "secondary image data" in some cases) (xi, yj) expressed by the rectangular coordinates system after coordinate conversion corresponds to which position of the coordinate system of the image data (hereinafter, referred to as "primary image data" in some cases) before the coordinate conversion.

FIG. 4A is a diagram illustrating the image data before coordinate conversion when the horizontal step is photographed. Generally, each of the sample points (ri, θj) of the primary image data I (ri, θj) before coordinate conversion is expressed by the polar coordinates system having an upper right end as the origin. In other words, the position of each of the sample points (ri, θj) is expressed by the polar coordinates system. For example, each of the sample points (ri, θj) is expressed by an angle θ of a scanning line and a length r from a rotation center to each of the sample points on the respective scanning lines.

In creating the table for conversion, an image area after the coordinate conversion into the rectangular coordinates system is set first. This image area can be set arbitrarily. For example, an allowable x-y domain is obtained from each of the sample points (ri, θj) according to the following Equation (1), and then the image area after the coordinate conversion may be set with reference to the domain.

[Equation 1]

$r = r_0 + r'$ $x = r \cos \theta$ $y = r \sin \theta$ (1)

From the image data obtained by an interference optical system, it is difficult to grasp the distance r between the rotation center of the fiber 4 and each of the sample points. If the distance r from the rotation center is not clear, it is not possible to perform the coordinate conversion according to Equation (2) described later. Therefore, in the example, a point at which a distance from the rotation center is clear is assumed to be a standard, and the distance r' between the standard and each of the sample points is measured. Then, the length r between the rotation center and the sample point is calculated by adding the length r0 between the rotation center and the standard, and the distance r' between the standard and the sample point.

In the example, the shielding area 64 is photographed as a line S1 (refer to FIG. 4A). Since the distance between the shielding area 64 and the rotation center of the fiber 4 is known in terms of design, in the example, the shielding area 64 on the image is assumed to be a standard and then the distance to each of the sample points is measured based on the standard. Accordingly, as illustrated in the equation (1), the distance r between the rotation center and the sample point is calculated by assuming that r0 is the distance between the rotation center of the fiber 4 and the shielding area 64 and r' is the distance between the shielding area 64 and the sample point.

Figure 5:
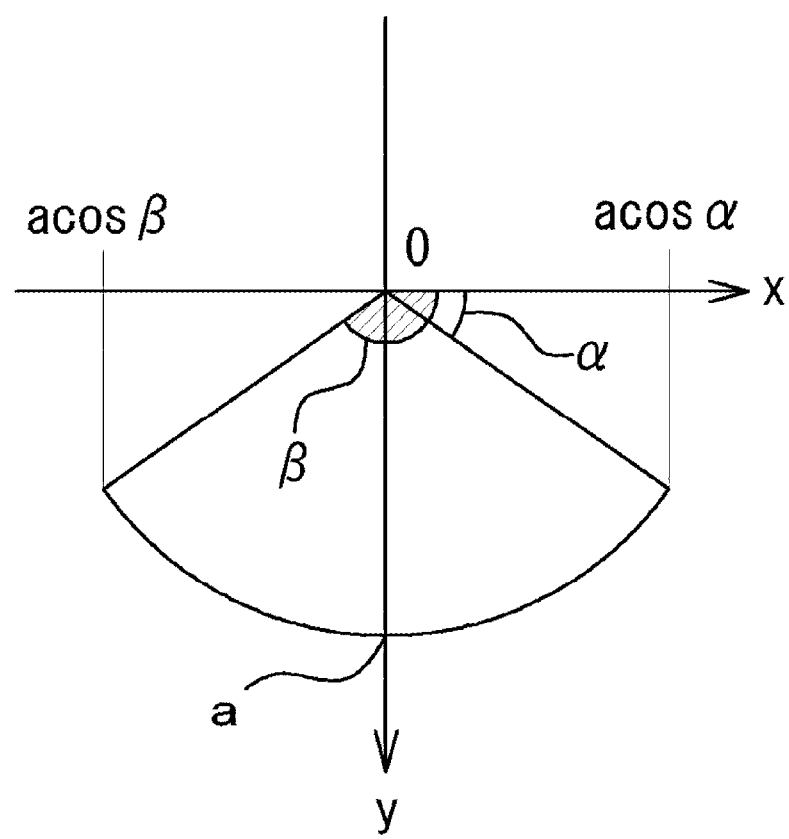
FIG. 5 is a diagram for explaining an equation used in the example.
Figure 6:
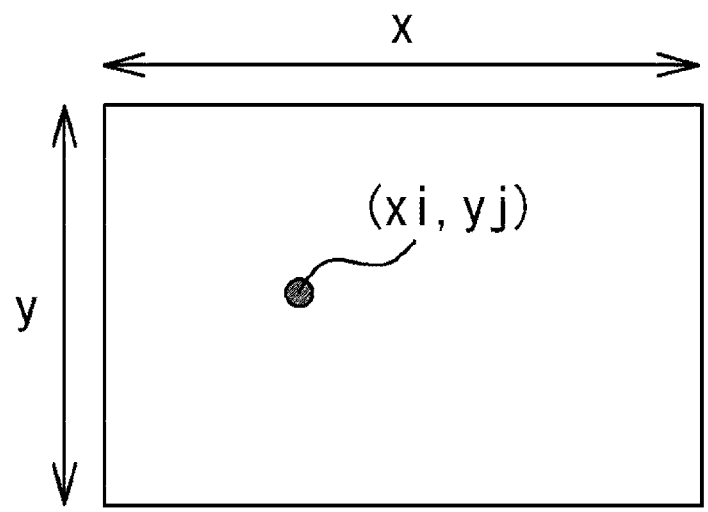
FIG. 6 is a diagram for explaining a process executed in the example.

FIG. 5 is a diagram illustrating an x-y domain calculated from equation (1), for example, in a case where r (depth of the image data) is in the range of 0≤r≤a and θ (the scanning angle of the fiber 4) is in the range of α≤θ≤β. The x-y domain satisfying the above conditions becomes in the range of axcos β≤x≤axcos α, and 0≤y≤a.

Figure 4B:
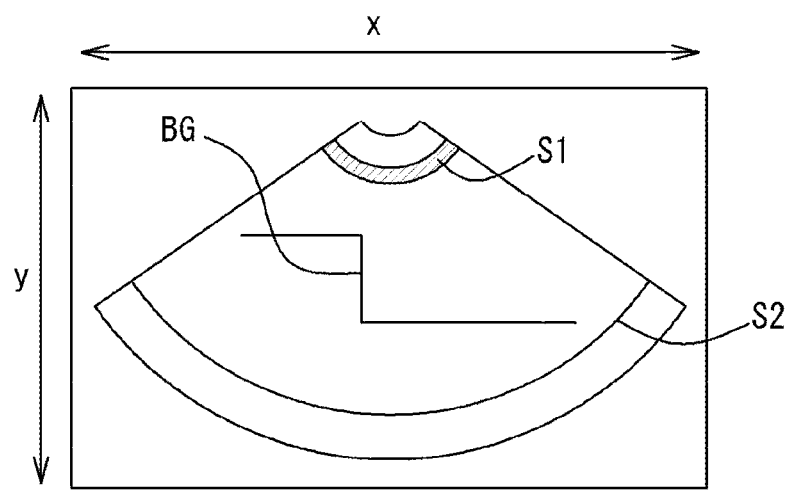

The image area after the coordinate conversion may be set to a range, for example, including all of the x-y domains or including some of x-y domains with reference to the calculated x-y domains. For example, the image area after the coordinate conversion as illustrated in FIG. 4B is set to a wide range compared to the x-y domain.

In this manner, the image area can be set to be sufficient for a required image area with respect to the polar coordinates data by setting the image area after the coordinate conversion in consideration of the x-y domain. In addition, it is possible to display, for example, the image with sufficient resolution by setting a portion of the x-y domain to the image area. Surely, the x-y domain is not necessarily calculated and the image area is not necessary to be set in consideration of the x-y domain.

Meanwhile, in the image area, the CPU 21 may be automatically set or may be set by an input of the inspector. The image area may be stored in the ROM in advance. In addition, as described above, for example, the x-y domain is calculated from the CPU 21 by inputting an allowable range of r and θ, and thus the x-y domain may be taken into consideration.

If the image area is set, which pixel (xi, yj) of the secondary image data I (xi, yj) in the set area image corresponds to which position of the polar coordinates system of the primary image data I (ri, θj) are calculated. The following equation (2) is an example of the equation for calculating the position of the primary image data I (ri, θj) with respect to the pixels (xi, yj).

[Equation 2]

$r = (x^2 + y^2)^{1/2}$ $\theta = \tan^{-1}(y/x)$ (2)

With respect to each of the pixels (xi, yj) of the secondary image data I (xi, yj), a corresponding position in the polar coordinates system is calculated according to the equation (2). Regarding the corresponding position as this calculation result, the sample point and the pixel may not be a one-to-one correspondence, but in this case, the value of each pixel may be interpolated from such values of the several sample points near the corresponding position.

Thus, the corresponding positions in the polar coordinate system for each pixel are calculated and then the calculated positions are written in the RAM 22 one after another. Therefore, the secondary image data I (xi, yj) is generated and then is read out from the RAM 22 to be displayed.

The image data (the primary image data) before the coordinate conversion is temporarily stored in the RAM 22. The CPU 21 generates the secondary image data I (xi, yj) corresponding to a pixel matrix of the display screen of the display unit 31 from the primary image data I (ri, θj) which is stored in the RAM 22. In a generation process of the secondary image data I (xi, yj), a correlation and an interpolation of the coordinates are required. The secondary image data I (xi, yj) generated from the CPU 21 is temporarily stored in the RAM 22 and then read out to the display unit 31.

In the example, the corresponding positions in the polar coordinate system, before coordinate conversion, corresponding to each of all pixels (xi, yj) of the secondary image data I (xi, yj) are calculated at least before the start of the measurement and stored in RAM 22 in advance.

<Measurement of Distance>

Next, a distance measuring method will be described by using the coordinate-converted image. In the image data after coordinate conversion, the actual distance with respect to the length of one pixel is determined. For example, when the number of pixels for photographing a range of 5 mm of image data obtained by the detector 18 is assumed to be 688 pixels, the actual distance per one pixel becomes 5/688 mm. Accordingly, it is possible to obtain the actual distance according to the number of pixels of a portion to be measured on distance.

Figure 7:
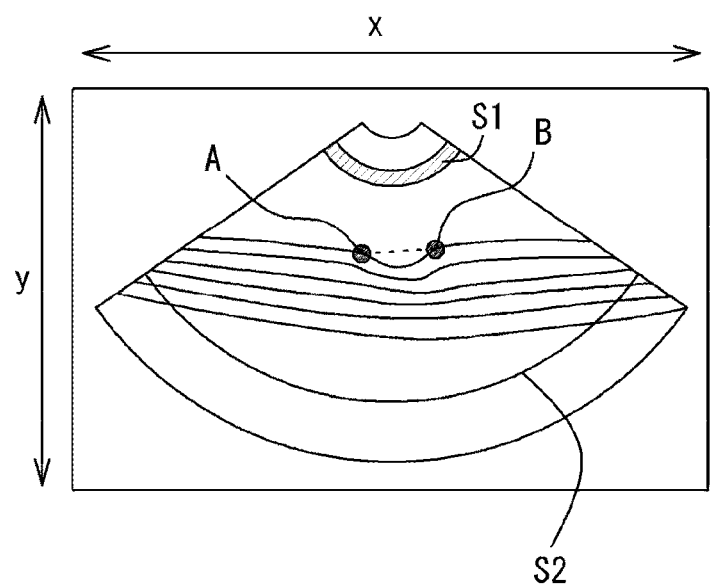
FIG. 7 is a diagram for explaining a method of measuring the length of an image in the example.

For example, as illustrated in FIG. 7, it is assumed that points A and B on the image after the coordinate conversion are given by the inspector. The CPU 21 measures the number of pixels included in the distance between the pixel of the specified point A and the pixel of the point B in the horizontal direction and in the vertical direction. As described above, since the actual distance is determined with respect to the length of one pixel, it is possible to measure the distance between the point A and the point B. Meanwhile, a segment AB connecting the point A and the point B is oblique with respect to the image, the distance between the point A and the point B may be calculated by the Pythagorean theorem.

<Operation Method and Control Operation of the Apparatus>

Subsequently, an operation method of the apparatus and a control operation of the apparatus will be described. First, the CPU 21 creates the table for conversion based on the size of the image area set as described above, and then stores the table for conversion in the RAM 22. It is preferable that the creation of the table for conversion be performed at least before the measurement.

After the table for conversion is stored in the RAM 22, the inspector manipulates the foot switch 35 by inserting the probe 2 into the object eye. The foot switch 35 outputs the operation signal to the CPU 21. The CPU 21 starts the measurement by receiving the operation signal from the foot switch 35.

The CPU 21 causes the measuring beam to be emitted from the measuring light source and causes the fiber 4 to rotate. The measuring beam passing through the fiber 4 is applied to the inside of the object eye from the transmission area and then reflected from a fundus of the eye. The measuring beam reflected from the fundus of the eye enters the inside the insertion portion 6 again from the transmission area to pass through the fiber 4. The measuring beam which is returned to the measuring unit by passing through the fiber 4 is combined with the reference beam from the reference optical system at the coupler 14 so as to become the interference beam, and the interference beam is detected by the detector 18.

According to a scanning angle θj of the primary image data and an address ri of the pixels of the primary light receiving elements detected by the detector 18 for each the scanning angle θ set in advance, the CPU 21 writes the image data into the RAM 22 one after another based on the table for conversion stored in the RAM 22.

The CPU 21 causes the display unit 31 to display, for example, the generated secondary image data. The inspector operates, for example, the foot switch 35 to capture the image which is being measured in real time. The CPU stores (records) the real time images in the non-volatile memory 24 as a still image when the operation signal is received from the foot switch 35. Then, the CPU 21 causes the display unit 31 to display the still image stored in the non-volatile memory 24 on the screen.

The inspector selects a part to be measured on the distance of the still image which is displayed on the display unit 31. For example, the inspector selects two points on the image by operating the operating unit 32. The CPU 21 measures the actual distance from the pixel numbers between two points as described above. The CPU 21 displays, for example, the measured actual distance between two points on the display unit 31.

Modification Example

Meanwhile, in the example, the shielding area 64 is assumed to be a standard, but the standard is not limited to the shielding area 64. As long as there is a point capable of being a standard on the image, the measurement may be performed by using the point as the standard. For example, in FIGS. 4 and 7, a line S2 is obtained by the measuring beam which is reflected from the optical member inside the probe and imaged on the tomographic image as a mirror image.

In this case, if the optical member from which the measuring beam is reflected is specified, it is possible to calculate the distance between each point and the rotation center of the fiber even with the line S2 as a standard. In this manner, the rotation center of the probe may be calculated through the reflected light inside the probe as a standard.

In addition, in the above description, the conversion of the image data is performed by calculating the position of the rotation center of the fiber from the positional information of the inside of the probe, but is not limited thereto. For example, the conversion of the image data may be performed based on the length information of an interference optical path.

For example, with respect to the probe having the standard length between the attaching unit 16 and the tip end (for example, the condensing portion 71), even in a case where the probe having a different length is attached, the rotation axis of the fiber 4 may be calculated by adjusting the reference mirror installed on the reference optical system 15 based on the difference of the length with respect to the probe having the standard length.

Meanwhile, in the above description, the table for conversion is created before measurement, but is not limited thereto. For example, the secondary image data may be calculated by substituting the acquired primary image data into the equation (2) instead of creating the table for conversion.

The table conversion is performed from the acquired image for each angle θ at all times, but is not limited thereto. For example, the conversion into the secondary image data may be performed by the table for conversion after the scanning is completed in the set scanning angle θ and data is completely acquired.

Meanwhile, in the example, the table for conversion is stored in the RAM 22, but is not limited thereto. For example, the table for conversion may be stored in the ROM 23 in advance, or may be stored in the non-volatile memory 24. In addition, the table for conversion may be created whenever the measurement is performed or one table for conversion may be used in a plurality of measurements. Further, a plurality of tables for conversion may be stored in the control unit 20.

What is claimed is:

1. An optical tomographic image photographing apparatus for acquiring information on a tissue inside a specimen in a depth direction, the apparatus comprising:
    a light source configured to emit a light beam;
    a dividing unit configured to divide the emitted optical flux into a measuring beam and a reference beam;
    an attaching unit to which a probe is to be attached, the probe being configured to irradiate an inside of the specimen with the measuring beam and rotatably scan the inside of the specimen with the measuring beam;
    a synthesis unit configured to generate a first interference beam by synthesizing the measuring beam reflected from the tissue inside the specimen and the reference beam;
    a detector configured to detect the generated first interference beam as a first interference signal, the first interference beam being detected for each scanning position of the measuring beam;
    a processor; and memory storing a computer executable program, when executed by the processor, causing the optical tomographic image photographing apparatus to execute:
  a tomographic image acquiring instruction of acquiring tomographic information for each scanning position of the specimen by using the detected first interference signal and acquiring tomographic image data of the specimen expressed by polar coordinates by using the tomographic information; and
  a coordinate conversion instruction of converting the tomographic image data of the specimen expressed by the acquired polar coordinates into image data expressed by rectangular coordinates; and
  wherein:
  the synthesis unit generates a second interference beam obtained by synthesizing the measuring beam reflected from the inside of the probe without being applied to the inside of the specimen and the reference beam,
  the detector detects, as a second interference signal, the second interference beam and the reference,
  the tomographic image acquiring instruction causes the optical tomographic image photographing apparatus to acquire positional information of the inside of the probe from which the measuring beam is reflected by using the second interference signal, and
  the coordinate conversion instruction causes the optical tomographic image photographing apparatus to acquire a shaft position of a rotation axis when the probe rotatably scans the inside of the specimen with the measuring beam by using the acquired positional information of the inside of the probe and convert the tomographic image data of the specimen expressed by the polar coordinates into the tomographic image data expressed by the rectangular coordinates by setting the position of the acquired rotation axis as an origin of the polar coordinates system.

2. The optical tomographic image photographing apparatus according to claim 1, wherein
  an optical fiber configured to guide the measuring beam and a shielding member configured to shield the measuring beam emitted from the optical fiber are disposed inside the probe, and
  the detector detects, as the second interference signal, the second interference beam generated by synthesizing the measuring beam which is reflected from the shielding member and the reference beam.

3. The optical tomographic image photographing apparatus according to claim 1, wherein
  an optical fiber configured to guide the measuring beam and an optical member configured to be coupled with the optical fiber and guide the measuring beam emitted from the optical fiber to the inside of the specimen are disposed inside the probe, and
  the detector detects, as the second interference signal, the second interference beam generated by synthesizing the measuring beam which is reflected from an interface between the optical fiber and the optical member and the reference beam.

4. The optical tomographic image photographing apparatus, according to claim 1, wherein the computer executable program when executed by the processor further causes the optical tomographic image photographing apparatus to execute a distance calculating instruction of calculating a distance between two points in the specimen based on the tomographic image data which is coordinate-converted by the coordinate conversion instruction.

5. The optical tomographic image photographing apparatus according to claim 1, further comprising a display unit configured to display a tomographic image,
  wherein the computer executable program when executed by the processor further causes the optical tomographic image photographing apparatus to execute a display control instruction of causing the display unit to display, as the tomographic image, the tomographic image data which is coordinate-converted into the rectangular coordinates.

6. A non-transitory computer readable recording medium storing a program for an optical tomographic image photographing apparatus which acquires information on a tissue inside a specimen in a depth direction, the optical tomographic image photographing apparatus including: an attaching unit to which the probe is attached; a synthesis unit configured to generate a first interference beam by synthesizing the measuring beam reflected from the tissue inside the specimen and the reference beam; a detector configured to detect the generated first interference beam as a first interference signal, the first interference beam being detected for each scanning position of the measuring beam; and a processor, the program when executed by the processor causing the optical tomographic image photographing apparatus to execute:
  a tomographic image acquiring instruction of acquiring tomographic information for each scanning position of the specimen by using the detected first interference signal and acquiring tomographic image data of the specimen expressed by polar coordinates by using the tomographic information; and
  a coordinate conversion instruction of converting the tomographic image data of the specimen expressed by the acquired polar coordinates into image data expressed by rectangular coordinates; and
  wherein:
  the synthesis unit generates a second interference beam obtained by synthesizing the measuring beam reflected from the inside of the probe without being applied to the inside of the specimen and the reference beam,
  the detector detects, as a second interference signal, the second interference beam and the reference,
  the tomographic image acquiring instruction causes the optical tomographic image photographing apparatus to acquire positional information of the inside of the probe from which the measuring beam is reflected by using the second interference signal, and
  the coordinate conversion instruction causes the optical tomographic image photographing apparatus to acquire a shaft position of a rotation axis when the probe rotatably scans the inside of the specimen with the measuring beam by using the acquired positional information of the inside of the probe and convert the tomographic image data of the specimen expressed by the polar coordinates into the tomographic image data expressed by the rectangular coordinates by setting the position of the acquired rotation axis as an origin of the polar coordinates system.

* * * * *